(12) United States Patent
Okitsu et al.

(10) Patent No.: US 8,865,424 B2
(45) Date of Patent: *Oct. 21, 2014

(54) ANTI-FDP MONOCLONAL ANTIBODY, FDP MEASUREMENT REAGENT AND REAGENT KIT USING SAME, AND FDP MEASUREMENT METHOD

(71) Applicants: Naoya Okitsu, Kobe (JP); Katsushi Kobayashi, Kobe (JP); Noriaki Nakajima, Kobe (JP); Masumi Murakami, Kobe (JP); Kouji Sakaguchi, Kobe (JP); Ayumi Asaeda, Kobe (JP); Mayumi Sugimoto, Kobe (JP)

(72) Inventors: Naoya Okitsu, Kobe (JP); Katsushi Kobayashi, Kobe (JP); Noriaki Nakajima, Kobe (JP); Masumi Murakami, Kobe (JP); Kouji Sakaguchi, Kobe (JP); Ayumi Asaeda, Kobe (JP); Mayumi Sugimoto, Kobe (JP)

(73) Assignee: Sysmex Corporation, Hyogo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/752,035

(22) Filed: Jan. 28, 2013

(65) Prior Publication Data

US 2013/0149793 A1    Jun. 13, 2013

Related U.S. Application Data

(63) Continuation of application No. PCT/JP2011/067327, filed on Jul. 28, 2011.

(30) Foreign Application Priority Data

Jul. 30, 2010 (JP) .................................. 2010-172222

(51) Int. Cl.
| | |
|---|---|
| G01N 33/546 | (2006.01) |
| G01N 33/68 | (2006.01) |
| G01N 33/86 | (2006.01) |
| C07K 16/34 | (2006.01) |
| C12Q 1/56 | (2006.01) |
| C07K 14/75 | (2006.01) |
| G01N 33/577 | (2006.01) |
| C07K 16/36 | (2006.01) |
| C07K 16/28 | (2006.01) |
| G01N 33/58 | (2006.01) |

(52) U.S. Cl.
CPC .......... *C07K 16/36* (2013.01); *G01N 2800/102* (2013.01); *G01N 2800/226* (2013.01); *G01N 2800/324* (2013.01); *C07K 14/75* (2013.01); *G01N 33/577* (2013.01); *G01N 2800/224* (2013.01); *C07K 16/2803* (2013.01); *G01N 33/6893* (2013.01); *G01N 33/586* (2013.01); *G01N 2333/75* (2013.01)

USPC .......... 435/13; 436/534; 436/501; 435/355; 530/388.25

(58) Field of Classification Search
None
See application file for complete search history.

(56) References Cited

U.S. PATENT DOCUMENTS

| | | | | |
|---|---|---|---|---|
| 4,208,479 | A | * | 6/1980 | Zuk et al. .................. 435/7.9 |
| 4,722,903 | A | | 2/1988 | Kudryk et al. |
| 4,851,334 | A | | 7/1989 | Kudryk et al. |
| 5,091,512 | A | * | 2/1992 | Gargan et al. .............. 436/518 |
| 5,821,068 | A | * | 10/1998 | Soe et al. .................. 435/7.21 |
| 2013/0011869 | A1 | * | 1/2013 | Nagahama et al. .......... 435/7.92 |

FOREIGN PATENT DOCUMENTS

| | | |
|---|---|---|
| DE | 4242736 | 6/1994 |
| EP | 0 842 949 A1 | 5/1998 |
| EP | 1 085 088 A1 | 3/2001 |
| JP | 60-166698 A | 8/1985 |
| JP | 60-185800 A | 9/1985 |
| JP | 05-038906 B2 | 6/1993 |
| JP | 07046104 | 2/1995 |
| JP | 11349600 | 12/1999 |
| JP | 2001-021557 A | 1/2001 |
| JP | 2001-354700 A | 12/2001 |
| JP | 2002-372536 A | 12/2002 |
| JP | 3472138 | 12/2003 |
| JP | 2006-105633 A | 4/2006 |
| JP | 2006105633 A * | 4/2006 |
| WO | WO 8801514 A1 * | 3/1988 |

OTHER PUBLICATIONS

Rudikoff et al., 1982, PNAS USA 79:1979-1983.*
Amit et al., 1986, Science 233:747-753.*
Gaffney, P. J., 1980, J. Clin. Pathol., 33(14):p. 10-17.*
Toda, Naoko O., "Nanopia P-FDP, a Plasma FDP Measurement Reagent," Japanese Journal of Clinical Laboratory Automation, 2002, pp. 327, vol. 27, No. 4.
Koppert et al., "Production and characterization of a monoclonal antibody reactive with a specific neoantigenic determinant (comprising BSS 54-118) in degradation products of fibrin and of fibrinogen", Blood, 68(2):437-441 (1986).
Nieuwenhuizen et al., "Plasma assay for derivatives of fibrin and of firbinogen, based on monoclonal antibodies", Fibrinolysis, 2(1):1-5 (1998).
Amiral et al, "Monoclonal antibodies to different neo-epitopes on fibrinogen and fibrin degradation products", Blood Coagulation & Fibrinolysis, 1(4/05):447-452 (1990).

* cited by examiner

*Primary Examiner* — Christine Foster
*Assistant Examiner* — Ellen J Marcsisin
(74) *Attorney, Agent, or Firm* — Sughrue Mion, PLLC

(57) ABSTRACT

The present invention relates to an anti-FDP monoclonal antibody selected from the first, second and third monoclonal antibodies having different reactivity towards FDP. The present invention also relates to a reagent and reagent kit for the measurement of FDP and a method for measurement of FDP using the anti-FDP monoclonal antibodies.

18 Claims, 1 Drawing Sheet

ANTI-FDP MONOCLONAL ANTIBODY, FDP MEASUREMENT REAGENT AND REAGENT KIT USING SAME, AND FDP MEASUREMENT METHOD

CROSS-REFERENCE TO RELATED APPLICATION

This application is a continuation of International Application PCT/JP2011/067327 filed on Jul. 28, 2011, which claims benefit of Japanese patent application JP 2010-172222 filed on Jul. 30, 2010, both of which are incorporated herein by reference in their entireties.

BACKGROUND OF THE INVENTION

The present invention relates to novel anti-FDP monoclonal antibodies which recognize fibrinogen and fibrin degradation products (FDP). The present invention also relates to a reagent and reagent kit for the measurement of FDP and a method for measurement of FDP using the antibodies.

When thrombi (stabilized fibrin) are formed in blood vessels or tissues due to hemostasis or other pathogenic causes, fibrinolysis is developed in vivo to remove the thrombi. The fibrinolysis for lysing thrombi is called secondary fibrinolysis in which fibrin in thrombi is degraded by enzymatic actions such as plasmin to produce fibrin degradation products (FbnDP: secondary fibrinolysis products) in blood. On the other hand, there is another fibrinolysis in vivo, called primary fibrinolysis, which is developed without association with formation of thrombi. During primary fibrinolysis, fibrinogen is degraded by enzymatic actions such as plasmin to produce fibrinogen degradation products (FbgDP: primary fibrinolysis products) in blood. These degradation products of fibrin and fibrinogen are collectively called as FDP (fibrinogen and fibrin degradation products).

The presence of FDP in blood can be an index for predicting in vivo hyperfibrinolysis. Due to this, the measurement of FDP in blood is used for diagnoses of diseases related to thrombi, cardiovascular disorders, hyperfibrinolysis, abnormal hemorrhage and the like or disseminated intravascular coagulation (DIC). Particularly, it is required to measure total FDP amount regardless of the type of FDP in order to classify pathological conditions of DIC.

Immunological approach has been conventionally applied for reagents for the measurement of blood FDP, and reagents utilizing turbidimetric immunoassay are commercially available, for example. Such reagents for the measurement of FDP include reagents using polyclonal antibodies such as anti-human fibrinogen antibodies. However, when FDP are measured with such reagents, the measured value of FDP may be falsely high unless a specimen to be measured is a biological sample of which fibrinogen has been deprived such as serum. However, the preparation of serum is complicated. In addition, because plasma is used as specimens for blood coagulation tests such as PT (prothrombin time), APTT (activated partial thromboplastin time), Fbg (fibrinogen concentration) and the like, reagents for the measurement of plasma FDP using monoclonal antibodies are clinically preferred in which plasma can be used as specimens (see Japanese Patent Publication Nos. Hei 5 (1993)-38906 and Hei 7 (1995)-46104, Japanese Patent No. 3472138 and Japanese Unexamined Patent Publication Nos. 2001-354700 and 2002-372536).

SUMMARY OF THE INVENTION

Reagents for the measurement of FDP using serum react equally with primary and secondary fibrinolysis products. However, it is observed that monoclonal antibodies used in conventional reagents for the measurement of plasma FDP have different reactivity towards primary and secondary fibrinolysis products. Namely, the conventional reagents for the measurement of plasma FDP tend to have higher reactivity towards secondary fibrinolysis products than towards primary fibrinolysis products.

In general, fibrinogen is not degraded under physiological conditions. Accordingly, secondary fibrinolysis products account for a major portion of FDP, making the above difference in reactivity less problem under normal measurements. However, biological samples obtained from patients suffering from DIC or acute promyelocytic leukemia, who are in such a condition that blood plasmin is hyperactivated to enhance primary fibrinolysis, contain primary fibrinolysis products. Thus, the total FDP amount in subjects with the condition of hyperfibrinolysis may not be measured accurately with conventional reagents for the measurement of plasma FDP having lower reactivity towards primary fibrinolysis products.

An object of the present invention is to provide anti-FDP monoclonal antibodies which have reactivity towards both primary and secondary fibrinolysis products. Another object of the present invention is to provide a reagent and reagent kit which use the antibodies to allow accurate measurement of FDP in subjects with the condition of hyperfibrinolysis. A further object of the present invention is to provide methods for measurement of FDP using the reagent and the reagent kit.

The present inventors have carried out extensive studies, prepared more than one anti-FDP monoclonal antibodies having different reactivity towards FDP and found that FDP can be measured with high accuracy even in biological samples containing primary fibrinolysis products by using a reagent containing a carrier sensitized with these antibodies, thereby completing the present invention.

Thus, the present invention provides an anti-FDP monoclonal antibody selected from the following three monoclonal antibodies:
  a first monoclonal antibody which reacts with fibrinogen and the fragments X, Y and D of primary fibrinolysis products among FDP as well as reacts with the fragments DD, DD/E and XDP of secondary fibrinolysis products among FDP;
  a second monoclonal antibody which does not react with fibrinogen but reacts with the fragments X, Y and E of primary fibrinolysis products among FDP as well as reacts with the fragments DD, DD/E and XDP of secondary fibrinolysis products among FDP; and
  a third monoclonal antibody which does not react with fibrinogen but reacts with the fragments Y and E of primary fibrinolysis products among FDP as well as reacts with the fragments DD, DD/E and XDP of secondary fibrinolysis products among FDP.

The present invention also provides a reagent for the measurement of FDP comprising a carrier sensitized with the first, second and third monoclonal antibodies.

The present invention also provides a reagent kit for the measurement of FDP comprising a first reagent containing a buffer and a second reagent containing a carrier sensitized with the first, second and third monoclonal antibodies.

The present invention further provides a method for measurement of FDP comprising the steps of:
  mixing a biological sample with a suspension of carrier particles sensitized with the first, second and third monoclonal antibodies; and
  measuring a degree of aggregation of the carrier particles resulting from antigen-antibody reaction.

The anti-FDP monoclonal antibodies of the present invention can provide a reagent, reagent kit and method which allow highly accurate measurement of FDP even in biological samples containing primary fibrinolysis products.

DETAILED DESCRIPTION OF THE EMBODIMENTS

Figure 1:
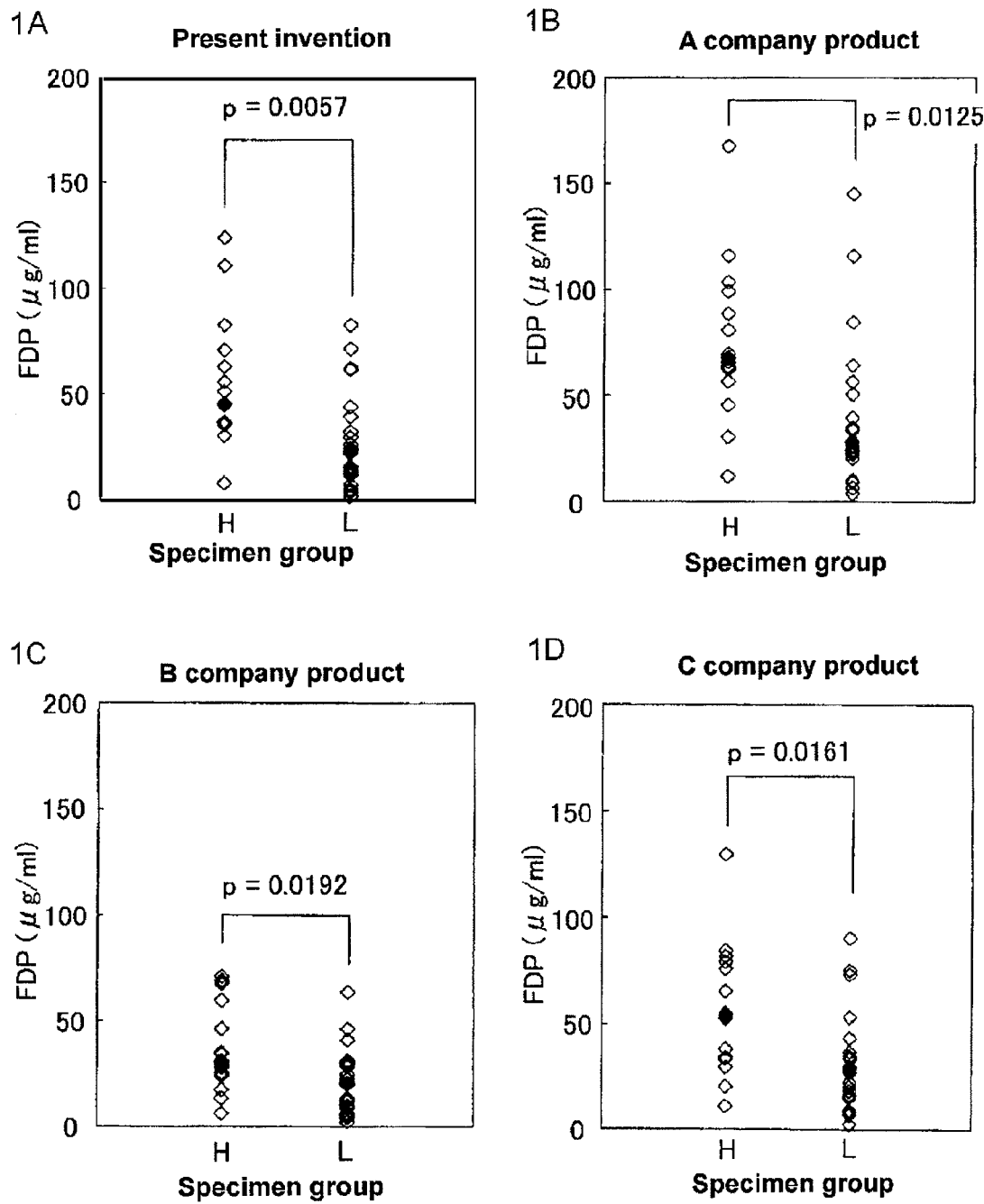
FIGS. 1A, 1B, 1C and 1D are the graphs showing the results of FDP concentration measurement on the specimen groups with "high hyperfibrinolysis" and "low hyperfibrinolysis".

As used herein, the term "FDP" means both fibrin degradation products and fibrinogen degradation products.

As used herein, the term "fibrin degradation products" is also referred to as secondary fibrinolysis products and corresponds to the a group of proteins produced by degradation of stabilized fibrin, which is a polymer formed after coagulation of fibrinogen in blood due to enzymatic actions of thrombin and the like, with enzymes such as plasmin and the like. The fibrin degradation products include the fragment DD, the fragment DD/E, the fragment XDP and the like. The fragment XDP includes polymers of the fragment DD/E, e.g., the fragment DXD/YY which is a trimer of the fragment DD/E; the fragment YXY/DXXD which is a pentamer of the fragment DD/E; and the fragment DXXD/YXXY which is a heptamer of the fragment DD/E. In the art, the fragment XDP is also referred to as the D dimer.

As used herein, the term "fibrinogen degradation products" is also referred to as primary fibrinolysis products and corresponds to a group of proteins produced by degradation of fibrinogen in blood with enzymes such as plasmin and the like. The fibrinogen degradation products include the fragment X, the fragment Y, the fragment D and the fragment E.

As used herein, the "reactivity towards FDP" is defined according to the type of FDP which specifically reacts with an anti-FDP monoclonal antibody. Thus, when an anti-FDP monoclonal antibody specifically reacts with a FDP which is of a different type to the type of FDP reacting with another anti-FDP monoclonal antibody, these antibodies are determined to have different reactivity towards FDP.

The anti-FDP monoclonal antibodies of the present invention are characterized in that they have different reactivity towards FDP and react with at least the fragment Y of the primary fibrinolysis products among FDP and the fragments DD, DD/E and XDP of the secondary fibrinolysis products among FDP. The three monoclonal antibodies are referred to as "the first monoclonal antibody", "the second monoclonal antibody" and "the third monoclonal antibody" hereinbelow.

The first monoclonal antibody is characterized in that it reacts with fibrinogen and the fragments X, Y and D of primary fibrinolysis products among FDP as well as reacts with the fragments DD, DD/E and XDP of secondary fibrinolysis products among FDP.

The second monoclonal antibody is characterized in that it does not react with fibrinogen but reacts with the fragments X, Y and E of primary fibrinolysis products among FDP as well as reacts with the fragments DD, DD/E and XDP of secondary fibrinolysis products among FDP.

The third monoclonal antibody is characterized in that it does not react with fibrinogen but reacts with the fragments Y and E of primary fibrinolysis products among FDP as well as reacts with the fragments DD, DD/E and XDP of secondary fibrinolysis products among FDP.

The first, second and third monoclonal antibodies may be any antibodies derived from mammals such as mouse, rat, hamster, rabbit, goat, horse and the like, among which mouse is preferred. The isotype of the antibodies may be any of IgG, IgM, IgE, IgA and the like. The antibodies include fragments and derivatives thereof, which may be exemplified by Fab fragments, F(ab')2 fragments and the like.

The first, second and third monoclonal antibodies can be obtained by immunological procedures known in the art. Namely, the monoclonal antibodies can be obtained by immunizing an animal with antigens, FDP (primary and/or secondary fibrinolysis products), and an adjuvant optionally mixed therewith, fusing B lymphocytes obtained from the animal with suitable myeloma cells to obtain hybridomas and purifying the antibodies from a culture supernatant of the hybridomas.

More specifically, the first, second and third monoclonal antibodies used for the present reagent can be obtained by the following method.

(Preparation of Antigens)

The antigens, FDP, can be obtained by reacting an enzyme capable of degrading fibrin and fibrinogen such as plasmin with fibrin and fibrinogen. The fibrin and fibrinogen, which are starting materials for FDP, are commercially available. Fibrin may also be obtained by reacting fibrinogen with thrombin, factor XIII and a calcium salt.

(Immunization)

The thus obtained antigens may be optionally mixed with an adjuvant and are dissolved or suspended in a suitable buffer to prepare an antigen solution, which can be then used for immunization of an animal. The concentration of the antigens in the antigen solution is preferably around 50 to 500 µg/ml. When the antigens have low immunogenicity, the antigens may be optionally linked to a carrier protein such as albumin, keyhole-limpet hemocyanin.

The adjuvant may be any adjuvant known in the art, which may include, for example, Freund's complete adjuvant (FCA), Freund's incomplete adjuvant (FIA), Ribi (MPL), Ribi (TDM), Ribi (MPL+TDM), *Bordetella pertussis* vaccine, muramyl dipeptide (MDP), aluminium adjuvant (ALUM) and combinations thereof. The particularly preferable combination is to use FCA for priming and FIA or Ribi adjuvants for boosting.

The animal to be immunized may be any of mouse, rat, hamster, horse, goat, rabbit and the like, among which mouse is preferred and BALB/c mouse is more preferred.

The method for immunization can be appropriately selected according to the type of antigens used or the presence or absence of an adjuvant. When a mouse is immunized, for example, the mouse is primed with 0.05 to 1 ml of an antigen solution mixed with an adjuvant (containing 10 to 200 µg of antigens) by an intraperitoneal, subcutaneous, intramuscular or tail vein injection followed by 1 to 4 boost immunizations at about every 4 to 21 days from the prime immunization and a final immunization at about 1 to 4 weeks thereafter. Immunization may be carried out with intraperitoneal injections of a high amount of antigen without an adjuvant in the antigen solution. Antibody titer is measured after 5 to 10 days of the boost immunization(s) by collecting blood. The antibody titer can be measured according to known methods in the art such as the antibody titer assay described hereinbelow. The spleen is recovered from the immunized animal after about 3 to 5 days of the final immunization, from which antibody producing cells can be obtained after separation of spleen cells.

(Preparation of Monoclonal Antibodies)

The monoclonal antibodies can be prepared according to any methods known in the art, for example a method described in Kohler and Milstein, Nature, 256, 495-497 (1975).

Myeloma cells which may be used are the cells derived from any mammals such as mouse, rat, human and the like including mouse myeloma cell lines P3X63-Ag8, P3X63-Ag8-U1, P3NS1-Ag4, SP2%-Ag14, P3X63-Ag8•653 and the like. When the myeloma cells used for fusion are those producing immunoglobulin light chains, the immunoglobulin heavy chains produced by the antibody producing cells may randomly bind to these light chains. Due to this, the myeloma cells which do not produce immunoglobulin light chains such as P3X63-Ag8•653, SP2%-Ag14 and the like are preferably used. It is preferable that the antibody producing cells and the myeloma cells are derived from allogeneic, particularly syngeneic animals.

The method for preparing hybridomas by fusing antibody producing cells and myeloma cells may include a method using polyethylene glycol (PEG), a method using Sendai virus, a method using an electrofusion apparatus and the like. When PEG is used, spleen cells and myeloma cells are suspended at a mixing ratio of 1 to 10:1, preferably 5 to 10:1 in an appropriate medium or buffer containing about 30 to 60% of PEG (average molecular weight: 1000 to 6000) and incubated under the conditions of a temperature of about 25 to 37° C. and pH of 6 to 8 for about 30 seconds to 3 minutes. After the incubation, cells are washed to remove the PEG-containing solution, resuspended in a medium, seeded on a microtiter-plate and cultured.

The thus fused cells are cultured on a selection medium to carry out selection of hybridomas. The selection medium may be the medium on which only fused cells can proliferate such as hypoxanthine-aminopterine-thymidine (HAT) medium. The selection of hybridomas can be generally carried out as follows: at 1 to 7 days after cell fusion, a part of, preferably about a half of the medium is exchanged to the selection medium, the cultivation is continued with the similar medium exchange at every 2 to 3 days and after completion of cultivation, wells in which hybridoma colonies are proliferated are selected under microscopic observation.

The thus obtained hybridomas may be confirmed whether or not they produce the desired antibody by carrying out the antibody titer assay on culture supernatant of the hybridomas. The antibody titer assay can be carried out according to the method known in the art. For example, the antibody can be detected by adding serial dilutions of the culture supernatant to an antigen protein immobilized on a solid phase and allowing reaction with a secondary antibody (anti-globulin antibody, anti-IgG antibody, anti-IgM antibody and the like) labeled with a fluorescent substance, enzyme or radioisotope (RI).

A single clone can be isolated from the hybridoma which is confirmed of its production of the desired antibody in the antibody titer assay by the limiting dilution analysis, the soft agar assay, a method using a fluorescence activated cell sorter and the like. In the limiting dilution analysis, for example, colonies of the hybridoma are serially diluted to around 1 cell/well in a medium before cultivation to isolate the hybridoma which produces the desired antibody.

The method for recovery of the monoclonal antibody from the hybridoma can be appropriately selected depending on the required amount of the monoclonal antibody or the properties of the hybridoma, which may include, for example, a method in which the monoclonal antibody is recovered from ascites of a mouse transplanted with the hybridoma, a method in which the monoclonal antibody is recovered from a cell culture supernatant and the like. The hybridoma which can proliferate intraperitoneally in mice can provide the monoclonal antibody with as high a concentration as several milligrams per ml of ascites. The hybridoma which can not proliferate in vivo can provide the monoclonal antibody from a cell culture supernatant. In this case, although the antibody production amount is low, purification is facilitated because of less contamination with immunoglobulins or other foreign substances.

When the antibody is obtained from the peritoneal cavity of a mouse transplanted with the hybridoma, a BALB/c mouse is preliminarily administered with an immunosuppressant such as pristane (2,6,10,14-tetramethyl pentadecane) and transplanted with the hybridoma (about $1 \times 10^6$ or more) before recovery of ascites after about 1 to 3 weeks. When heterogeneous hybridoma is transplanted, nude mice or radiation treated mice are preferably used.

When the antibody is obtained from a cell culture supernatant, the hybridoma may be cultivated, for example, by static culture which is used for cell maintenance as well as by a high density cultivation method or the spinner flask cultivation method and the culture supernatant containing the antibody can be obtained. It is preferable that the amount of serum in the medium is as low as possible because the addition of serum to the medium may cause contamination of foreign substances such as other antibodies and albumin to make purification of the antibody complicated. It is preferable that the hybridoma is adapted to a serum-free medium by the conventional method and is cultivated in the serum-free medium. This may facilitate the purification of the antibody.

The monoclonal antibody can be purified from ascites or a culture supernatant according to the method known in the art which may include, for example, the methods based on a fractionation method based on salt precipitation using salts such as ammonium sulfate, sodium sulfate and the like, a polyethylene glycol fractionation method, an ethanol fractionation method, DEAD ion-exchange chromatography, gel filtration chromatography and the like.

When the target antibody is murine IgG, the antibody can be purified with affinity chromatography using a Protein A-conjugated carrier or an anti-mouse immunoglobulin-conjugated carrier.

Among the anti-FDP monoclonal antibodies of the present invention, the first monoclonal antibody may include, for example, an antibody (hereinafter also referred to as "FDP3-2920 antibody") produced by a hybridoma "FDP3-2920" which was deposited with Incorporated Administrative Agency National Institute of Technology and Evaluation Patent Microorganisms Depositary (2-5-8 Kazusakamatari, Kisarazu-shi, Chiba 292-0818 Japan) on Jun. 1, 2010 under the accession number of NITE BP-949.

The second monoclonal antibody may include, for example, an antibody (hereinafter also referred to as "FDP3-797 antibody") produced by a hybridoma "FDP3-797" which was deposited with Incorporated Administrative Agency National Institute of Technology and Evaluation Patent Microorganisms Depositary (2-5-8 Kazusakamatari, Kisarazu-shi, Chiba 292-0818 Japan) on Jun. 1, 2010 under the accession number of NITE BP-950.

The third monoclonal antibody may include, for example, an antibody (hereinafter also referred to as "FDP3-2935 antibody") produced by a hybridoma "FDP3-2935" which was deposited with Incorporated Administrative Agency National Institute of Technology and Evaluation Patent Microorganisms Depositary (2-5-8 Kazusakamatari, Kisarazu-shi, Chiba 292-0818 Japan) on Jun. 1, 2010 under the accession number of NITE BP-951.

The ratio of concentration between the first, second and third monoclonal antibodies in the reagent for the measurement of FDP of the present invention (hereinafter also referred to as the present reagent) is not particularly limited and can be appropriately selected by a person skilled in the art.

The present reagent comprises a carrier sensitized with the first, second and third monoclonal antibodies. The carrier may include organic polymeric compounds, inorganic compounds, erythrocytes and the like. The organic polymeric compounds may include insoluble agaroses, insoluble dextrans, celluloses, latexes, polystyrenes, styrene-methacrylic acid copolymers, styrene-glycidyl(meth)acrylate copolymers, styrene-styrene sulfonate copolymers, methacrylic acid polymers, acrylic acid polymers, acrylonitrile-butadiene-styrene copolymers, vinyl chloride-acrylic ester copolymers, poly(vinyl acetate-acrylates) and the like. The inorganic compounds may include silica, alumina and the like.

The shape of the carrier is not particularly limited and may be any shape of spherical, planar and the like. When the carrier is spherical, the average diameter of the carrier particles can be appropriately selected depending on measurement instruments and may appropriately be 0.05 to 0.5 μm in general. The material of the particles is particularly preferably latex.

The first, second and third monoclonal antibodies may be linked to the carrier particles according to any of physical adsorption and chemical binding methods known in the art, among which physical adsorption methods are preferred because the procedures are simple.

When the carrier is particles, the carrier particles may be carrier particles each being sensitized with three, i.e., the first, second and third monoclonal antibodies, or may be a mixture of carrier particles respectively sensitized with each monoclonal antibody. When the first, second and third monoclonal antibodies have different sensitization conditions to a carrier particle, these antibodies preferably sensitize carrier particles separately.

When the carrier particles are latex particles, the carrier particles sensitized with the first, second and third monoclonal antibodies are suspended in an appropriate buffer. The concentration of latex particles in the suspension is preferably 0.5 to 10 mg/ml and more preferably 0.75 to 5 mg/ml. The total concentration of the monoclonal antibodies in the suspension is preferably 10 to 100 μg/ml and more preferably 20 to 50 μg/ml.

The buffer may include the buffer which has a buffering action at pH 5 to 10 and preferably pH 6 to 9. Specifically, the buffer may include, for example, phosphate buffers, imidazole buffers, triethanolamine-hydrochloric acid, Good's buffers and the like. Good's buffers may include MES, Bis-Tris, ADA, PIPES, Bis-Tris-Propane, ACES, MOPS, MOPSO, BES, TES, HEPES, HEPPS, Tricine, Tris, Bicine, TAPS and the like buffers. Among these, MOPSO is preferred.

The buffer may further comprise additives such as protein stabilizers (e.g., BSA and the like), preservatives (e.g., sodium azide, phenylmethanesulfonyl fluoride and the like), pH modifiers, sensitizers (e.g., polyvinylpyrrolidone, polyanions, polyethylene glycols, polysaccharides and the like), inorganic salts (e.g., sodium chloride, calcium chloride and the like), background reducing agents (e.g., human anti-mouse antibody (HAMA) absorbing agents and the like).

An embodiment of the present reagent may include a reagent kit for the measurement of FDP (hereinafter also referred to as the present reagent kit). The present reagent kit comprises a first reagent containing a buffer and a second reagent containing a suspension of carrier particles sensitized with the first, second and third monoclonal antibodies.

The present reagent kit is the reagent kit for detecting FDP in a biological sample based on immunoassay, for example, an assay (latex agglutination) in which latex particles sensitized with the above first, second and third monoclonal antibodies and FDP in the sample are reacted.

Examples of the first, second and third monoclonal antibodies which are used in the present reagent kit may include FDP3-2920, FDP3-797 and FDP3-2935 antibodies, respectively.

The present reagent kit is of a two-reagent type consisting of the first and second reagents as described above. However, the present reagent kit may be of a one-reagent type consisting of one reagent. In view of the measurement accuracy, the reagent kit is preferably of a two-reagent type consisting of the first and second reagents. More preferably, the present reagent kit is in the form comprising the first reagent containing the buffer and the second reagent consisting of the reagent for the measurement of FDP of the present invention.

The buffer which may be used for the first reagent constituting the present reagent kit may include the same buffers which may be used for suspending the carrier particles in the present reagent. The first reagent may contain protein stabilizers, preservatives, pH modifiers, sensitizers, inorganic salts and the like as described above.

The method for measurement of FDP of the present invention can be carried out with the reagent or reagent kit for the measurement of FDP of the present invention. As an embodiment of the method for measurement of FDP of the present invention, the method for measurement of FDP in a biological sample with the reagent kit for the measurement of FDP of the present invention is specifically described hereinbelow.

The first reagent containing the buffer and a biological sample are first mixed and incubated. The biological sample may include serum, plasma, urine and the like which are obtained from a subject. The first reagent and the biological sample may be mixed at a volume ratio of about 5:1 to 50:1. The incubation may be carried out for about 1 to 10 minutes.

The mixture of the first reagent and the biological sample is then added with the second reagent containing a suspension of carrier particles sensitized with the first, second and third monoclonal antibodies. The mixture and the second reagent may be mixed at a volume ratio of about 1:0.05 to 1:1.5.

When the second reagent is added and mixed, FDP and the carrier particles in the second reagent are aggregated because of antigen-antibody reaction. The degree of the aggregation is measured as the amount of change in absorbance per minute. This measurement is preferably carried out on an optical instrument which can measure scattered light intensity, absorbance or transmitted light intensity. The measurement wavelength may be appropriately selected from the range of 300 to 2400 nm, preferably 300 to 1000 nm and more preferably 500 to 1000 nm.

The concentration and/or amount of FDP in the biological sample can be calculated from the measured amount of change in absorbance based on a calibration curve prepared by measurements of the FDP standard substance having known concentrations.

The present reagent kit may also be applied for a method in which the first and second reagents are mixed prior to addition of a biological sample to the mixture of these reagents and optical measurement of the degree of aggregation of carrier particles.

Examples of the first, second and third monoclonal antibodies which are used in the present method for measurement of FDP may include FDP3-2920, FDP3-797 and FDP3-2935 antibodies, respectively.

Examples are described hereinbelow, which do not limit the present invention.

EXAMPLES

Example 1

Generation of Hybridomas Producing Anti-FDP Monoclonal Antibodies and Preparation of the Antibodies (1) Preparation of Immunogens (Antigens)
(1-1) Preparation of Primary Fibrinolysis Antigen To 241 mg (39.7 mg/ml) of fibrinogen (Sigma) was added plasmin (Sigma) to a final concentration of 60 mU/ml and incubated at 37° C. for 8 hours. Aprotinin was then added to a final concentration of 1 U/ml to terminate the degradation reaction. The obtained reaction solution was centrifuged at 12,000×g for 20 minutes, the obtained supernatant was subjected to chromatography on a lysine-Sepharose 4B column (volume: 8 ml) equilibrated with a 50 mM Tris buffer (pH 7.4) followed by removal of Sepharose on a spin column.

The obtained solution was exchanged twice to a sample buffer (62.5 mM Tris, 192 mM glycine and 1% SDS (pH 6.8)) with an ultrafiltration centrifuge tube (Amicon 15 50K; Millipore). The obtained solution was charged into Sephacryl S-300 (GE Healthcare) at a flow rate of 70 to 80 µl/min with a peristaltic pump and fractions were collected every 10 minutes. The respective fractions obtained were analyzed on SDS-PAGE with molecular weight markers to recover the fractions containing the fragment X, fragment Y and fragment D.

The recovered fractions were charged into Sephacryl S-300 (GE Healthcare) at a flow rate of 2 ml/min with a peristaltic pump and fractions were collected every 30 seconds. The obtained fractions were analyzed on SDS-PAGE as described above to recover the fractions containing the high-molecular weight fragment (fragments X and Y) of the primary fibrinolysis products. The fractions were exchanged twice to a phosphate buffer (PBS) with Amicon 15 50K (Millipore) to obtain a primary fibrinolysis antigen.

(1-2) Preparation of Secondary Fibrinolysis Antigen

To 92 mg (23 mg/ml) of fibrinogen (Sigma) were added calcium chloride, human thrombin (Mitsubishi Pharma Corporation) and factor XIII (Nipro) at final concentrations of 25 mM, 4 U/ml and 0.05 U/ml, respectively and incubated at 37° C. for overnight to convert fibrinogen to fibrin. The generated fibrin gel in the reaction solution was washed with 50 ml of Tris buffer (TBS (pH 7.4)) and centrifuged at 4° C., 3,000×g for 10 minutes to collect the fibrin gel. The same procedure was repeated twice followed by grinding the fibrin gel with a 50-ml syringe. The fibrin gel was resuspended in 4.6 ml of TBS (pH 7.4). The suspension was added with plasmin to a final concentration of 75 mU/ml and incubated at 37° C. for 6 hours. Aprotinin was then added to a final concentration of 1 U/ml to terminate the degradation reaction.

The obtained reaction solution was centrifuged at 12,000×g for 20 minutes, the obtained supernatant was subjected to chromatography on a lysine-Sepharose 4B column (volume: 3.5 ml) equilibrated with a 50 mM Tris buffer (pH 7.4) followed by removal of Sepharose on a spin column.

The obtained solution was exchanged three times to a sample buffer (62.5 mM Tris, 192 mM glycine and 1% SDS (pH 6.8)) with an ultrafiltration centrifuge tube (Amicon 15 50K; Millipore). The obtained solution was charged into Sephacryl S-300 (GE Healthcare) at a flow rate of 2 ml/min with a peristaltic pump and fractions were collected every 30 seconds. The respective fractions obtained were analyzed on SDS-PAGE with molecular weight markers to recover the fractions containing the fragment XDP, fragment DD/E, fragment DD and fragment E.

The recovered fractions were charged into Sephacryl S-300 (GE Healthcare) at a flow rate of 2 ml/min with a peristaltic pump and fractions were collected every 30 seconds. The obtained fractions were analyzed on SDS-PAGE as described above to recover the fractions containing the fragments DD/E and DD. The fractions were exchanged twice to a phosphate buffer (PBS) with Amicon 15 50K (Millipore) to obtain a secondary fibrinolysis antigen.

(2) Administration of Antigens to Animals

The animals to be immunized were 5-week-old inbred BALB/c female mice (Charles River Laboratories Japan Inc.). The mice were kept in an animal breeding cage (23±1° C., humidity: 70%) with standard pellets while allowing them to reach water freely.

The antigens prepared in the above (1-1) and (1-2) were respectively diluted in PBS to obtain antigen solutions at 200 µg/ml. Each antigen solution (0.5 ml) and the same amount of Freund's complete adjuvant (Difco) were mixed and emulsified. The emulsified antigens (200 µl) were respectively administered to four 5-week-old BALB/c female mice intraperitoneally. The 100 µg/ml antigens with Ribi adjuvant were further administered to mice every 2 weeks in total four times at 20 µg each. One month after the fourth administration, booster immunization was carried out with the 100 µg/ml antigens with Ribi adjuvant, followed by measurement of mouse antibody titer according to the method described hereinbelow. Mice with high antibody titer received a final immunization after 2 weeks by tail vein administration of the 100 µg/ml antigens in PBS.

(3) Antibody Titration

A small amount of blood was collected regularly after initiation of immunization from mouse retinal fundus and serum was separated from the pooled blood. The obtained serum was analyzed for antibody titer against fibrin and fibrinogen degradation products according to the following method.

The antigen solutions prepared in the above (1-1) and (1-2) were diluted in PBS to 10 µg/ml, dispensed into the wells of 96-well microtiterplates at 100 µl/well and left to stand at 4° C. for 18 hours. The wells were washed three times with 10 mM phosphate buffer (pH 7.0) containing 0.05% Tween 20 (hereinafter referred to as the washing solution). The wells were then filled with 10 mM phosphate buffer containing 1% BSA (hereinafter referred to as the blocking buffer) to obtain primary and secondary fibrinolysis antigen solid phases.

The serum (20 µl) and 80 0 of the blocking buffer were added in the wells of the antigen solid phases and incubated at room temperature for one hour. After the incubation, the wells were washed five times with the washing solution, respectively added with 100 µl of a POD labeled anti-mouse IgG antibody (DAKO) diluted to 1/2000 in the blocking buffer and incubated at room temperature for 30 minutes. After the incubation, the wells were washed five times with the washing solution, respectively added with 100 µl of an ODP substrate solution (International Reagents Co., Ltd.) and incubated at room temperature for 15 minutes. The wells were then respectively added with 100 µl of 2N sulfuric acid to terminate the reaction and absorbance was measured at 490 nm.

Serum obtained from non-immunized mice was used as a negative control and added instead of the above serum.

(4) Cell Fusion

The spleen was recovered from the BALB/c mice three days after the final immunization and spleen cells were dispersed in the EMEM medium. The spleen cells were washed four times in the EMEM medium followed by cell count to obtain $7.0 \times 10^8$ spleen cells.

The parent cell line used for cell fusion was a myeloma culture cell line derived from BALB/c mouse which is resistant to 8-azaguanine (2-amino-6-oxy-8-azapurine) (P3X63-Ag8•653; hereinafter referred to as the "X63 cells"). The X63 cells were passaged in the RPMI-1640 medium containing 10% inactivated fetal calf serum (FCS) (containing 20 µg/ml 8-azaguanine). From three days prior to cell fusion, the cells were cultivated in the 10% FCS-containing RPMI-1640 medium without 8-azaguanine in order to use the X63 cells in the logarithmic growth phase. The X63 cells were washed in the RPMI-1640 medium three times followed by cell count to obtain $7.0 \times 10^7$ cells.

Polyethylene glycol 4000 was dissolved in the RPMI-1640 medium to 50 (w/v) % and the above spleen cells and the X63 cells were mixed in the obtained medium so as to obtain the cell number ratio of 10:1. The cells were fused on an electrofusion apparatus SSH-2 (Shimadzu Corporation). The cell fusion was carried out under the conditions of 10-second application of alternating voltage (40V) followed by application of direct current pulse (2.3 kV/cm, pulse width: 40 µsec) to the mixture of the spleen cells and myeloma cells.

The fused cells were suspended in the HAT selection medium containing $1 \times 10^{-4}$M hypoxanthine, $4 \times 10^{-7}$M aminopterine and $1.6 \times 10^{-5}$M thymidine (HAT) in the 10% FCS-containing RPMI-1640 medium at $2.0 \times 10^6$ cells/ml. The cell suspension was dispensed into wells of a 96-well microtiterplate at 50 µl/well, followed by cultivation in a $CO_2$ incubator in the atmosphere of the temperature of 37° C., humidity of 95% and 8% $CO_2$. On day 1 and day 2 after the start of the cultivation, one drop of the HAT selection medium was added to the wells. On day 7 and day 9, two drops of the HAT selection medium were added to the wells and the cultivation was continued. After about 10 days to 2 weeks, the medium was replaced by the medium without HAT to obtain hybridomas.

(5) Screening of Hybridomas (5-1) Primary Screening

Among the hybridomas thus obtained, the strains which produce antibodies having reactivity towards respective primary and secondary fibrinolysis antigens were selected according to the method described below.

To the wells of the antigen solid phases used in the above (3) were added 20 µl of the hybridoma culture supernatant and 80 µl of the blocking buffer and incubated at room temperature for one hour. After the incubation, the wells were washed five times with the washing solution, respectively added with 100 µl of a POD labeled anti-mouse IgG antibody (DAKO) diluted to 1/2000 in the blocking buffer and incubated at room temperature for 30 minutes. After the incubation, the wells were washed five times with the washing solution, respectively added with 100 µl of an ODP substrate solution (International Reagents Co., Ltd.) and incubated at room temperature for 15 minutes. The wells were then respectively added with 100 µl of 2N sulfuric acid to terminate the reaction and absorbance was measured at 490 nm. The culture medium was used as a negative control and added instead of the hybridoma culture supernatant.

Based on the results of the measurements, the hybridomas producing the antibody having reactivity towards the high molecular weight fragment of the primary fibrinolysis products and the hybridomas producing the antibody having reactivity towards the fragments DD/E and DD were selected.

(5-2) Secondary Screening

The hybridomas selected in the primary screening were subjected to cloning based on the limiting dilution analysis, and the hybridoma which stably produces the antibody having reactivity towards the high molecular weight fragment of the primary fibrinolysis products (one clone: hereinafter referred to as "FDP3-2920") and the hybridomas which stably produce the antibody having reactivity towards the fragments DD/E and DD (two clones: hereinafter respectively referred to as "FDP3-797" and "FDP3-2935") were selected.

These FDP3-2920, FDP3-797 and FDP3-2935 were deposited with Incorporated Administrative Agency National Institute of Technology and Evaluation Patent Microorganisms Depositary (2-5-8 Kazusakamatari, Kisarazu-shi, Chiba 292-0818 Japan) on Jun. 1, 2010 under the accession numbers of NITE BP-949, NITE BP-950 and NITE BP-951, respectively.

(6) Purification of Monoclonal Antibodies from Ascites (6-1) Preparation of Ascites The above hybridomas ($1 \times 10^7$ cells/animal) were respectively inoculated intraperitoneally to 6-week-old female BALB/c nude mice (Charles River Laboratories Japan Inc.). After one week from the inoculation, the mice were boosted with the hybridomas ($1 \times 10^7$ cells/animal). After two weeks from the booster, ascites was collected from the mice with a syringe. Five mice were used for each hybridoma.

(6-2) Ammonium Sulfate Salt Precipitation

To 17.5 ml of the obtained ascites were added small portions of ammonium sulfate of the amount so as to obtain 50% saturation and stirred while cooling to obtain precipitation. The precipitation was then recovered and dissolved in PBS to obtain a solution. The obtained solution was dialyzed in a dialysis tube against 4 L PBS for 12 days. After dialysis, the solution in the tube was filtered through a 0.45-µm filter to obtain purified monoclonal antibodies.

The antibody obtained from the hybridoma FDP3-2920 was used as the first monoclonal antibody (hereinafter referred to as the FDP3-2920 antibody). The antibody obtained from the hybridoma FDP3-797 was used as the second monoclonal antibody (hereinafter referred to as the FDP3-797 antibody). The antibody obtained from the hybridoma FDP3-2935 was used as the third monoclonal antibody (hereinafter referred to as the FDP3-2935 antibody).

(7) Studies on Reactivity of Monoclonal Antibodies

The difference in reactivity of the first, second and third monoclonal antibodies, FDP3-2920, FDP3-797 and FDP3-2935 antibodies, respectively, towards fibrin and fibrinogen degradation products was studied by ELISA as follows.

(7-1) Preparation of Fibrinogen Degradation Products (FbgDP)

To 241 mg (39.7 mg/ml) of fibrinogen (Sigma) was added plasmin (Sigma) to a final concentration of 60 mU/ml and incubated at 37° C. for 8 hours. Aprotinin was then added to a final concentration of 1 U/ml to terminate the degradation reaction. The obtained reaction solution was centrifuged at 12,000×g for 20 minutes, the obtained supernatant was subjected to chromatography on a lysine-Sepharose 4B column (volume: 8 ml) equilibrated with a 50 mM Tris buffer (pH 7.4) followed by removal of Sepharose on a spin column to prepare a FbgDP solution. The protein concentration of the obtained FbgDP solution was measured with a protein quantification reagent (Bio-Rad). A part of the FbgDP solution was used for evaluation of reactivity towards FDP of the reagent for the measurement of FDP of the present invention as described hereinbelow.

The obtained FbgDP solution was exchanged twice to a sample buffer (62.5 mM Tris, 192 mM glycine and 1% SDS (pH 6.8)) with an ultrafiltration centrifuge tube (Amicon 15 50K; Millipore). The obtained solution was charged into Sephacryl S-300 (GE Healthcare) at a flow rate of 70 to 80 μl/min with a peristaltic pump and fractions were collected every 10 minutes. The respective fractions obtained were analyzed on SDS-PAGE with molecular weight markers to recover the fractions respectively containing the fragment X, fragment Y, fragment D and fragment E. The fractions were exchanged twice to a phosphate buffer (PBS) with Amicon 15 50K (Millipore) to obtain FbgDP antigens.

(7-2) Preparation of Fibrin Degradation Products (FbnDP)

To 92 mg (23 mg/ml) of fibrinogen (Sigma) were added calcium chloride, human thrombin (Mitsubishi Pharma Corporation) and factor XIII (Nipro) at final concentrations of 25 mM, 4 U/ml and 0.05 U/ml, respectively and incubated at 37° C. for overnight to convert fibrinogen to fibrin. The generated fibrin gel in the reaction solution was washed with 50 ml of Tris buffer (TBS (pH 7.4)) and centrifuged at 4° C., 3,000×g for 10 minutes to collect the fibrin gel. The same procedure was repeated twice followed by grinding the fibrin gel with a 50-ml syringe. The fibrin gel was resuspended in 4.6 ml of TBS (pH 7.4). The suspension was added with plasmin to a final concentration of 75 mU/ml and incubated at 37° C. for 6 hours. Aprotinin was then added to a final concentration of 1 U/ml to terminate the degradation reaction. The obtained reaction solution was centrifuged at 12,000×g for 20 minutes, the obtained supernatant was subjected to chromatography on a lysine-Sepharose 4B column (volume: 3.5 ml) equilibrated with a 50 mM Tris buffer (pH 7.4) followed by removal of Sepharose on a spin column to prepare a FbnDP solution. The protein concentration of the obtained FbnDP solution was measured with a protein quantification reagent (Bio-Rad). A part of the FbnDP solution was used for evaluation of reactivity towards FDP of the reagent for the measurement of FDP of the present invention as described hereinbelow.

The obtained FbnDP solution was exchanged three times to a sample buffer (62.5 mM Tris, 192 mM glycine and 1% SDS (pH 6.8)) with an ultrafiltration centrifuge tube (Amicon 15 50K; Millipore). The obtained solution was charged into Sephacryl S-300 (GE Healthcare) at a flow rate of 2 ml/min with a peristaltic pump and fractions were collected every 30 seconds. The respective fractions obtained were analyzed on SDS-PAGE with molecular weight markers to recover the fractions respectively containing the fragment XDP, fragment DD/E and fragment DD. The fractions were exchanged twice to a phosphate buffer (PBS) with Amicon 15 50K (Millipore) to obtain FbnDP antigens.

(7-3) Preparation of Fibrinogen Antigen

The fibrinogen antigen used was the fibrinogen solution (50 mg/ml) obtained by dissolving fibrinogen in TBS.

(7-4) ELISA Analysis

Respective anti-FDP monoclonal antibody solutions were diluted to 0.5 μg/ml in PBS, dispensed into the wells of 96-well microtiterplates at 100 μl/well and left to stand at 4° C. for 18 hours. The wells were washed three times with 10 mM phosphate buffer (pH 7.0) containing 0.05% Tween 20 (hereinafter referred to as the washing solution). The wells were then filled with 10 mM phosphate buffer containing 1% BSA (hereinafter referred to as the blocking buffer) to obtain antibody solid phases of anti-FDP monoclonal antibodies.

After the wells were washed three times with the washing solution, the wells of antibody solid phases were added with 100 μl of the respective FbgDP antigens and FbnDP antigens prepared as described above and incubated at room temperature for 30 minutes. After the incubation, the wells were washed three times with the washing solution, respectively added with 100 μl of a peroxidase-labeled anti-fibrinogen antibody (DAKO) and incubated at room temperature for one hour. After the incubation, the wells were washed three times with the washing solution, respectively added with 100 μl of an ODP substrate solution (International Reagents Co., Ltd.) and incubated at room temperature for 15 minutes. The wells were then respectively added with 100 μl of 2N sulfuric acid to terminate the reaction and absorbance was measured at 490 nm.

The results of ELISA are shown in Table 1. In Table 1, "+" denotes that the antibody has reactivity with the fragment and "+" denotes that the antibody has no reactivity with the fragment.

TABLE 1

| | | FDP3-2920 | FDP3-797 | FDP3-2935 |
|---|---|---|---|---|
| Non-FDP | Fibrinogen | + | − | − |
| Primary fibrinolysis products | Fragment X | + | + | − |
| | Fragment Y | + | + | + |
| | Fragment D | + | − | − |
| | Fragment E | − | + | + |
| Secondary fibrinolysis products | Fragment XDP | + | + | + |
| | Fragment DD/E | + | + | + |
| | Fragment DD | + | + | + |

Table 1 shows that the FDP3-2920, FDP3-797 and FDP3-2935 antibodies have different reactivity towards FDP.

More specifically:
the FDP3-2920 antibody reacts with fibrinogen and the fragments X, Y and D of primary fibrinolysis products among FDP as well as reacts with the fragments DD, DD/E and XDP of secondary fibrinolysis products among FDP;
the FDP3-797 antibody does not react with fibrinogen but reacts with the fragments X, Y and E of primary fibrinolysis products among FDP as well as reacts with the fragments DD, DD/E and XDP of secondary fibrinolysis products among FDP; and
the FDP3-2935 antibody does not react with fibrinogen but reacts with the fragments Y and E of primary fibrinolysis products among FDP as well as reacts with the fragments DD, DD/E and XDP of secondary fibrinolysis products among FDP.

Example 2

Preparation of Reagent and Reagent Kit for the Measurement of FDP (1) Production of the First Reagent Containing Buffer The reagents were mixed at the final concentrations shown in Table 2, adjusted to pH 7.1 with 1M sodium hydroxide aqueous solution and adjusted to 1 liter with ultrapure water to produce a buffer.

TABLE 2

| Reagents | Final conc. | Manufacturer |
|---|---|---|
| MOPSO | 75.5 mM | Dojindo Laboratories |
| Sodium chloride | 225 mM | Manac Inc. |
| Sodium azide | 0.10% | Kishida Chemical Co., Ltd. |
| BSA | 0.5% | PROLIANT |
| Ultrapure water | q.s. | |

(2) Production of Reagent for the Measurement of FDP Containing Suspension of Carrier Particles Sensitized with Anti-FDP Monoclonal Antibodies (2-1) Sensitization of Latex Particles with FDP3-2920 Antibody The FDP3-2920 antibody was mixed with a 50 mM 2-hydroxy-3-morpholinopropanesulfonic acid/150 mM NaCl solution to a final concentration of 1 mg/ml. This mixture was mixed with a 20% (weight ratio) latex suspension (particle diameter: 0.238 µm; JSR Corporation).

The obtained mixture was mixed with an equivalent amount of a 50 mM 2-hydroxy-3-morpholinopropanesulfonic acid/150 mM NaCl/2% BSA solution, followed by centrifugation at 10° C., 38,400×g for 30 minutes. The supernatant was removed and the obtained precipitate was added with a 50 mM 2-hydroxy-3-morpholinopropanesulfonic acid/150 mM NaCl/2% BSA/1.5% sucrose solution at the amount equivalent to the supernatant.

The obtained mixture was subjected to sonication under ice-cold conditions on an ultrasonic grinder (Otake Seisakusho K.K.) and an ultrasonic processor (equivalent to UP-200S from Dr. Hielscher GmbH) to obtain a suspension of latex particles sensitized with the FDP3-2920 antibody (antibody concentration: 39 µg/ml).

(2-2) Sensitization of Latex Particles with FDP3-797 Antibody

The FDP3-797 antibody was mixed with a 50 mM 2-hydroxy-3-morpholinopropanesulfonic acid/150 mM NaCl solution to a final concentration of 1 mg/ml. A suspension of latex particles sensitized with the FDP3-797 antibody (antibody concentration: 39 µg/ml) was obtained in the same manner as described in the above "(2-1) Sensitization of latex particles with FDP3-2920 antibody".

(2-3) Sensitization of Latex Particles with FDP3-2935 Antibody

The FDP3-2935 antibody was mixed with a 50 mM 2-hydroxy-3-morpholinopropanesulfonic acid/150 mM NaCl solution to a final concentration of 1 mg/ml. A suspension of latex particles sensitized with the FDP3-2935 antibody (antibody concentration: 39 µg/ml) was obtained in the same manner as described in the above "(2-1) Sensitization of latex particles with FDP3-2920 antibody".

(2-4) Production of Second Reagent

Equal amounts of the suspensions of latex particles sensitized with the FDP3-2920, FDP3-797 and FDP3-2935 antibodies were mixed to obtain the reagent for the measurement of FDP containing carrier particles sensitized with three monoclonal antibodies. This reagent for the measurement of FDP was hereinafter used as the second reagent.

In order to study the difference in reactivity of the FDP3-797 antibody and the FDP3-2935 antibody towards FDP, equal amounts of the suspensions of latex particles sensitized with the FDP3-797 and FDP3-2935 antibodies were mixed to obtain a reagent for the measurement of FDP containing carrier particles sensitized with two monoclonal antibodies.

Example 3

Evaluation of Reactivity of Reagent Kit for the Measurement of FDP of the Present Invention Towards FDP The reagent kit for the measurement of FDP of the present invention obtained in the above Example 2 and other company products were used to measure FDP in plasma.

The first reagent of the reagent kit for the measurement of FDP of the present invention was the reagent prepared in the above Example 2 (1). The second reagent was the reagent prepared in the above Example 2 (2). The mixing proportion (volume ratio) of the suspensions of latex particles respectively sensitized with each antibody was 1:1:1.

To a panel of plasma having high values of FDP (Golden West Biologicals, Inc.) was added a SDS-PAGE sample buffer (10% glycerol, 2% SDS and 62.5 mM Tris-HCl (pH 6.8) containing 0.01% BPB) to prepare samples, which were separated by SDS-PAGE. The separated proteins were transferred onto a PVDF membrane which was then subjected to Western blotting with an anti-human fibrinogen rabbit polyclonal antibody. According to the result of the Western blotting, the amount of primary fibrinolysis fragment containing the fragment D was analyzed in order to divide the panel of plasma into two groups, i.e., the "high hyperfibrinolysis" group having a high value for the primary fibrinolysis fragment and the "low hyperfibrinolysis" group including the plasma other than those in the high hyperfibrinolysis group.

The panel of plasma were used as the specimens. Each specimen (6 µl) was mixed with 84 µl of the first reagent and incubated at 37° C. for 20 seconds. The obtained reaction solution was mixed with 84 µl of the second reagent to initiate latex agglutination reaction. For other company products A to C, reagents were similarly mixed with the panel of plasma according to the instructions attached to these products to initiate latex agglutination reaction. Absorbance at the wavelength of 800 nm at 1 minute and 2 minutes after the initiation of the reaction was measured with CS-2000i (Sysmex Corporation). From the measurement results, the amount of change in absorbance per minute was obtained for each group, from which the FDP concentration was calculated. The results of measurements were analyzed for the significant difference between two groups. The results are shown in FIGS. 1A to 1D. In FIGS. 1A to 1D, the specimen group H represents the high hyperfibrinolysis group and the specimen group L represents the low hyperfibrinolysis group. the symbol ♦ denotes the median.

FIGS. 1A to 1D show that the significance probability of the reagent for the measurement of FDP of the present invention was less than 0.01 (p=0.0057) while the significance probability of other company products was 0.01 or more. Therefore, it was found that the reagent kit for the measurement of FDP of the present invention can differentiate plasma with high hyperfibrinolysis from plasma with low hyperfibrinolysis.

Therefore, it is demonstrated that the reagent and reagent kit for the measurement of FDP of the present invention can measure with higher accuracy the FDP concentration even in specimens obtained from subjects with the condition of hyperfibrinolysis than other company products.

What is claimed is:

1. A detection reagent for the measurement of Fibrin Degradation Product (FDP) comprising:

a first carrier having a first monoclonal antibody or an antigen binding fragment thereof, wherein the first monoclonal antibody or antigen binding fragment thereof does not bind a fragment E primary fibrinolysis product of FDP but binds to fibrinogen, a fragment X primary fibrinolysis product of FDP, a fragment Y primary fibrinolysis product of FDP, a fragment D primary fibrinolysis product of FDP, a fragment DD secondary fibrinolysis product of FDP, a fragment DD/E secondary fibrinolysis product of FDP, and to a fragment XDP secondary fibrinolysis product of FDP;

a second carrier having a second monoclonal antibody or an antigen binding fragment thereof, wherein the second monoclonal antibody is produced by the hybridoma having accession number NITE BP-950; and a third carrier having a third monoclonal antibody or an antigen binding fragment thereof, wherein the third monoclonal antibody or fragment thereof does not bind the fibrinogen, the fragment X primary fibrinolysis product of FDP, or a fragment D primary fibrinolysis product of FDP, but binds to a fragment Y primary fibrinolysis product of FDP, the fragment E primary fibrinolysis product of FDP, the fragment DD secondary fibrinolysis product of FDP, the fragment DD/E secondary fibrinolysis product of FDP, and to a XDP secondary fibrinolysis product of FDP.

2. The reagent of claim 1, wherein the first, second and third carriers are carrier particles.

3. The reagent of claim 1, wherein the first monoclonal antibody is the monoclonal antibody produced by the hybridoma having the accession number NITE BP-949 or an antigen binding fragment thereof.

4. The reagent of claim 1, wherein the third monoclonal antibody is the monoclonal antibody produced by the hybridoma having the accession number of NITE BP-951 or an antigen binding fragment thereof.

5. The reagent of claim 2, wherein the carrier particles are about 0.05 to 0.5 micron.

6. A method for measuring Fibrin Degradation Product (FDP) comprising the steps of:

Obtaining a biological sample;

Mixing said biological sample with the detection reagent of claim 1;

and measuring aggregation, thereby detecting the FDP.

7. The method of claim 6, wherein the aggression is measured based on a change in a optical absorbance.

8. The method of claim 6, wherein the biological sample is selected from the group consisting of serum, plasma, and urine.

9. The method of claim 6, wherein the measuring step involves detecting an amount of change in absorbance per minute.

10. The method of claim 9, wherein the measuring step is performed by an optical instrument.

11. The method of claim 9, wherein a scattered light intensity, an absorbance or a transmitted light intensity is measured.

12. The method of claim 11, wherein the change in absorbance per minute is measured at a wavelength in the range of 300 to 2400 nm.

13. The method of claim 12, wherein the wavelength is in the range of 300-1000 nm.

14. The method of claim 13, wherein the wavelength is in the range of 500-1000 nm.

15. The method of claim 6, wherein first, second and third carriers are particles mixed in a ratio of about 1:1:1.

16. The method of claim 6, wherein the measuring step comprises detecting an absorbance at a wavelength of 800 nm for 1 minute to 2 minutes.

17. A kit for the measurement of FDP comprising: a buffer; and the detection reagent of claim 1.

18. An anti-FDP monoclonal antibody selected from the group consisting of the following three monoclonal antibodies:

the monoclonal antibody produced by the hybridoma having accession number NITE BP-949;

the monoclonal antibody produced by the hybridoma having accession number NITE BP-950; and the monoclonal antibody produced by the hybridoma having accession number NITE BP-951.

* * * * *